US00PP34767P2

(12) United States Plant Patent
Horvath

(10) Patent No.: US PP34,767 P2
(45) Date of Patent: Nov. 22, 2022

(54) ***SEDUM SPURIUM* PLANT NAMED 'ROCK CANDY'**

(50) Latin Name: *Sedum spurium*
Varietal Denomination: Rock Candy

(71) Applicant: Brent Arpad Horvath, Fontana, WI (US)

(72) Inventor: Brent Arpad Horvath, Fontana, WI (US)

( * ) Notice: Subject to any disclaimer, the term of this patent is extended or adjusted under 35 U.S.C. 154(b) by 0 days.

(21) Appl. No.: 17/300,951

(22) Filed: Dec. 22, 2021

(51) Int. Cl.
*A01H 5/12* (2018.01)
*A01H 6/32* (2018.01)

(52) U.S. Cl.
USPC ..... Plt./479
CPC ..... *A01H 6/328* (2018.05)

(58) Field of Classification Search
USPC ..... Plt./479
CPC ..... A01H 5/02; A01H 5/12
See application file for complete search history.

(56) References Cited

PUBLICATIONS https://www.intrinsicperennialgardens.com/about-us/press/sedum-spurium-rock-candy-ppaf/; Apr. 6, 2021; 1 page.*

* cited by examiner

*Primary Examiner* — Kent L Bell

(57) ABSTRACT

A new, distinct *Sedum spurium* plant named 'Rock Candy' as illustrated and described, herein.

1 Drawing Sheet

Latin name: *Sedum spurium.*
Cultivar name: 'Rock Candy'.

BACKGROUND OF THE INVENTION

The present invention relates to a new and distinct *Sedum spurium* plant named 'Rock Candy' characterized by smaller, dark green and purple foliage, compared to the all green foliage of the parent plant. The new *Sedum spurium* was raised as an open pollinated seedling of a *Sedum spurium* 'John Creech', not patented, in Hebron, Ill. in 2018 as part of an ongoing breeding program. The selection of the new plant was due to its' smaller dark green and purple foliage, compared to the green foliage of the parent plant. Initial asexual reproduction has taken place at a nursery in Hebron, Ill. since 2019 by means of division, and vegetative cuttings. The new *Sedum spurium* has shown to be stable and identical in reproduction after rooting over 1000 plants from 2019 to 2020. No plants of the new *Sedum spurium* have been sold in this country, or anywhere in the world, prior to the filing of this application, nor has any disclosure of the new plant been made prior to the filing of this application with the exception of that which was disclosed by the inventor and his company, Intrinsic Perennial Gardens, Inc within one year of filing of this application and was derived directly from the inventor.

SUMMARY OF THE INVENTION

The new *Sedum spurium* plant named 'Rock Candy' characterized by smaller, dark green RHS 147 B and purple foliage RHS N79 A and N79 B, compared to the all green foliage of the parent plant, have been observed to be unique and stable.

Plants of the new *Sedum spurium* plant named 'Rock Candy' can be compared to plants of *Sedum spurium* 'John Creech', not patented. 1. The new *Sedum spurium* plant has smaller, dark green RHS 147 B and purple foliage RHS N79 A and N79 B, compared to the all green foliage of the parent plant.

Plants of the new *Sedum spurium* can be compared to plants of *Sedum spurium* 'Fuldaglut', not patented. 1. The new *Sedum spurium* plant has smaller, dark green RHS 147 B and purple foliage RHS N79 A and N79 B, compared to the foliage colors of 'Fuldaglut' RHS 147 C and 185 A. 2. The new *Sedum spurium* plant has smaller foliage measuring 1 cm in length and 8 mm in width while *Sedum spurium* 'Fuldaglut' has foliage measuring 15 mm in length and 12 wan in width. 3. Plants of the new *Sedum spurium* also grow denser.

Plants of the new *Sedum spurium* can be compared to plants of *Sedum spurium* 'Red Rock' not patented. 1. The new *Sedum spurium* plant has smaller, dark green RHS 147 B and purple foliage RHS N79 A and N79 B, compared to the foliage colors of 'Red Rock' RHS 187 A-D. 2. The new *Sedum spurium* plant has smaller foliage measuring 1 cm in length and 8 mm in width while *Sedum spurium* 'Red Rock' has foliage measuring 15 mm in length and 12 mm in width. 3. Plants of the new *Sedum spurium* also grow denser.

DESCRIPTION OF PHOTOGRAPHS

Figure 1:
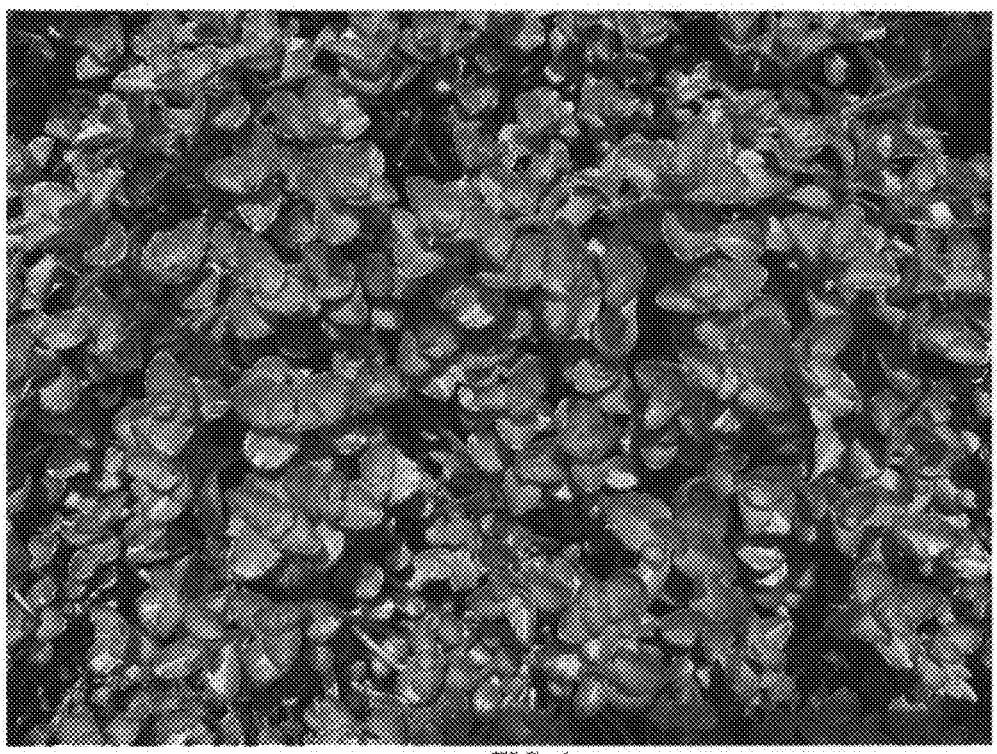
Figure 2:
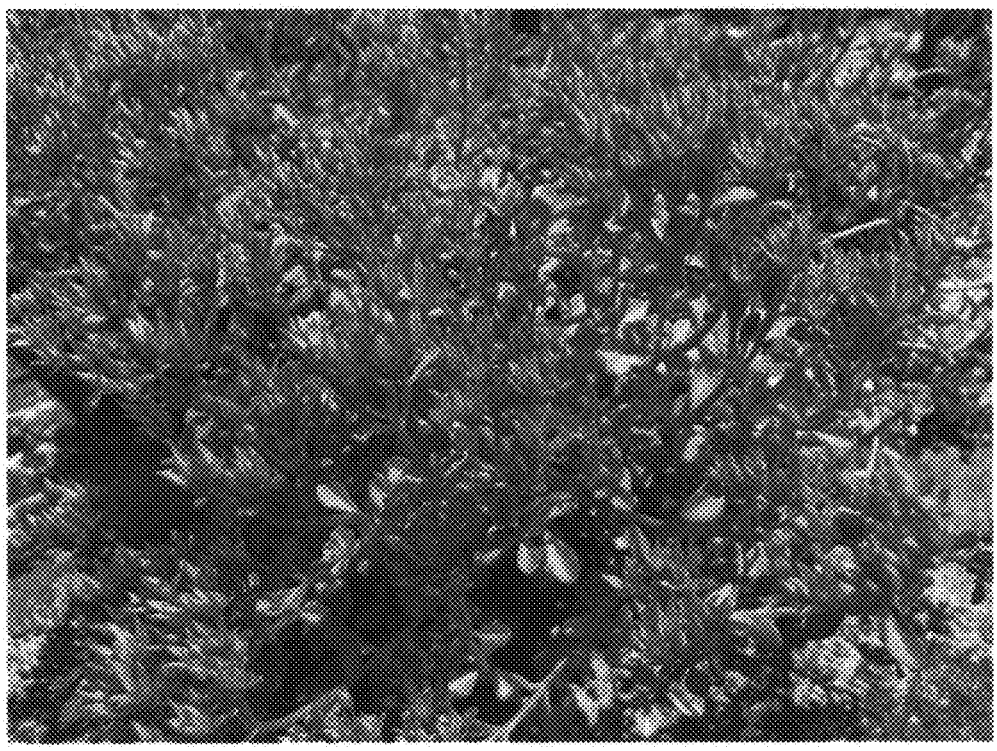

Plants pictured in the drawing wore grown for one year.
FIG. 1. Close up of the foliage.
FIG. 2. A picture of a blooming plant.

DETAILED BOTANICAL DESCRIPTION

In the following description, color references are made to The Royal Horticultural Society Colour Chart (2001). Plants used for the description were grown for one year. Measurements and numerical values represent averages of typical plants.

Botanical classification: *Sedum spurium* cultivar Rock Candy.

Parentage: Female parent *Sedum spurium* 'John Creech'. Male or pollen parent an unknown *Sedum spurium.*

Propagation: Vegetative division and cutting propagation.

Plant description: Overall habit of the new *Sedum spurium* is basal clumps, with upright stems topped by rose colored flowers in July.

*Plant height.*—Average 9-10 cm.
*Plant width.*—30 cm.
*Stem color.*—199 C in spring, summer, and fall.
*Stem shape.*—Both typical and observed — round.
*Stem texture.*—Glabrous.
*Stem length.*—12 cm.
*Stem diameter.*—3-4 mm.
*Internode length.*—5 cm.

Foliage, both, typical and observed:

*Type.*—Deciduous.
*Shape.*—Obovate..
*Petiole.*—None
*Length.*—1 cm.
*Width.*—8 mm.
*Thickness.*—1-2 mm.
*Margin.*—Crenate.
*Leaf apex, typical and observed.*—Obtuse.
*Leaf bases, typical and observed.*—Cuneate.
*Texture.*—Smooth.
*Leaf arrangement.*—Alternate, crowded except at the base of the stems.
*Leaf venation pattern.*—None noticed.
*Leaf vein color.*—None noticed.
*Adaxial leaf description.*—Color is 147 B at the center and N97 A and N97 B on the edge of the leaf.
*Abaxial leaf description.*—Color is 147 B at the center and N77 A on the edge of the leaf.
*Fall and winter foliage.*—Color is 147 B at the center and N77 A. on the edge of the leaf.

Flower, both, typical and observed:

*Petal count.*—5.
*Petal shape.*—Lanceolate.
*Adaxial petal color.*—N74 C. Adaxial Petal texture — glabrous.
*Abaxial petal color.*—N74 A. Abaxial Petal texture — glabrous.
*Petal apex shape.*—Acuminate.
*Petal base.*—2-3 mm wide.
*Petal length.*—6 mm.
*Petal width.*—2-3 mm.
*Petal margin, typical and observed.*—Entire.
*Petal bases, typical and observed.*—Obtuse.
*Inflorescence type.*—Panicle on basal flowering stems.
*Panicle color.*—N74 B.
*Individual flower size.*—11 mm across, 5 mm tall.
*Inflorescence size.*—Length and width — 3 cm across, 2 cm tall.
*Flower number.*—Approximately 50 per stem and 1000 per plant per season.
*Flower longevity of the inflorescence.*—3 to 4 weeks.
*Flower longevity of the individual flower.*—5 to 7 days.
*Flower shape.*—Stellate.
*Bloom period and duration.*—July.
*Bud shape, typical and observed.*—Elliptical.
*Bud length, typical and observed.*—4 mm.
*Bud diameter, typical and observed.*—3 mm.
*Bud color, typical and observed.*—Close to N74 D.
*Sepal size.*—1 mm across, 3 mm long.
*Sepal number.*—5.
*Sepal shape, typical and observed.*—Narrow ovate.
*Sepal apex, typical and observed.*—Acute.
*Sepal margin, typical and observed.*—Entire.
*Sepal color, abaxial and adaxial typical and observed.*—Close to N74 C and N74 D.
*Peduncle length, typical and observed.*—6 mm.
*Peduncle diameter, typical and observed.*—1 mm.
*Peduncle color, typical and observed.*—Close to 73 B.
*Peduncle texture, typical and observed.*—Glabrous.
*Pedicel length, typical and observed.*—6 mm.
*Pedicel diameter, typical and observed.*—1 mm.
*Pedicel color, typical and observed.*—Close to 73 B.
*Pedicel texture, typical and observed.*—Glabrous.
*Carpel color.*—N74 B and N74 C.
*Carpel surfaces.*—Glabrous.
*Stigma shape.*—Capitate.
*Stigma size.*—2 mm.
*Stigma typical and observed color.*—N74 C.
*Style length.*—1 mm.
*Style shape.*—Slender.
*Style typical and observed color.*—N74 C.
*Ovary size.*—1-2 mm.
*Ovary shape.*—Cordate.
*Ovary typical and observed color.*—N74 C.
*Fertility.*—10 anthers, 10 stamens.
*Anther color.*—12 A, Anther shape — ovate.
*Pollen color.*—Close to 17 B. Pollen amount — moderate.
*Filament color typical and observed.*—N74 C.
*Pistil number typical and observed.*—5.
*Pistil length typical and observed.*—5 mm.
*Blooming habit.*—Terminal panicle on up to 12 cm stems.
*Scent.*—No scent noticed.
*Fruit.*—None.
*Hardiness.*—U.S.D.A. hardiness zones 4-9.
*Disease resistance.*—Resistance to diseases common to *Sedum* has not been observed on plants grown under nursery conditions.
*Pest resistance.*—Resistance to pests common to *Sedum* has not been observed on plants grown under nursery conditions.

I claim:

1. A new, distinct *Sedum spurium* plant named 'Rock Candy' as illustrated and described, herein.

* * * * *